United States Patent
Chen et al.

(10) Patent No.: US 10,308,633 B2
(45) Date of Patent: Jun. 4, 2019

(54) PROCESS FOR MAKING M1 RECEPTOR POSITIVE ALLOSTERIC MODULATORS

(71) Applicant: Merck Sharp & Dohme Corp., Rahway, NJ (US)

(72) Inventors: Qinghao Chen, Edison, NJ (US); Shane W. Krska, New Providence, NJ (US); Lushi Tan, Edison, NJ (US); Peter E. Maligres, Fanwood, NJ (US); Jeremy Scott, Hertfordshire (GB); Carl Baxter, Hertfordshire (GB); Gavin William Stewart, Hertfordshire (GB); Andrew Gibb, Hertfordshire (GB)

(73) Assignees: Merck Sharp & Dohme Corp., Rahway, NJ (US); Merck Sharp & Dohme Limited, Hoddesdon, Hertfordshire ( * ) Notice: Subject to any disclaimer, the term of this patent is extended or adjusted under 35 U.S.C. 154(b) by 0 days.

(21) Appl. No.: 15/761,754

(22) PCT Filed: Sep. 26, 2016

(86) PCT No.: PCT/US2016/053652
§ 371 (c)(1),
(2) Date: Mar. 20, 2018

(87) PCT Pub. No.: WO2017/058691
PCT Pub. Date: Apr. 6, 2017

(65) Prior Publication Data
US 2018/0265493 A1     Sep. 20, 2018

Related U.S. Application Data

(60) Provisional application No. 62/235,061, filed on Sep. 30, 2015.

(51) Int. Cl.
*C07D 239/70* (2006.01)
*C07D 401/06* (2006.01)
*C07D 401/10* (2006.01)
*A61K 31/517* (2006.01)
*A61P 25/28* (2006.01)

(52) U.S. Cl.
CPC ................. *C07D 401/06* (2013.01)

(58) Field of Classification Search
CPC ... C07D 239/70; C07D 401/06; C07D 401/10
USPC .......................................... 544/249
See application file for complete search history.

(56) References Cited

U.S. PATENT DOCUMENTS

| | | |
|---|---|---|
| 2011/0224198 A1 | 9/2011 | Kuduk et al. |
| 2012/0196845 A1 | 8/2012 | Beshore et al. |
| 2013/0109686 A1 | 5/2013 | Beshore et al. |
| 2013/0184298 A1 | 7/2013 | Kuduk et al. |

FOREIGN PATENT DOCUMENTS

| | | |
|---|---|---|
| WO | WO2010059773 | 5/2010 |
| WO | 20170588689 A1 | 4/2017 |

OTHER PUBLICATIONS

Abdul-Ridha et al., echanistic Insights into Allosteric Structure-Function Relationships at the M1 Muscarinic Acetylcholine Receptor, J. of Biological Chemistry, 2014, pp. 33701-33711, 289 (48).
Abraham Fisher, Therapeutic Strategies in Alzheimer's Disease: M1 Muscarinic Agonists, Jpn. J. Pharmacol., 2000, pp. 101-112, 84.
Eglen, Therapeutic Opportunties from Muscarinic Receptor Research, Trends in Pharmacological Sciences, Aug. 2001, 409-414, 8.
Yang et al., Total Synthesis of 3,4-Dihydrobenzo[h] quinazolin-4-one and structure elucidation of perlolidine and samoquasine A, Tetrahedron Letters, 2003, pp. 319-322, 44.

*Primary Examiner* — Brenda L Coleman
(74) *Attorney, Agent, or Firm* — Sylvia A. Ayler; John C. Todaro

(57) ABSTRACT

This invention provides novel processes for the preparation of compounds such as 3-[(1S,2S)-2-hydroxycyclohexyl]-6-[(6-methylpyridin-3-yl)methyl]benzo[h]-quinazolin-4(3H)-one, salts and derivatives thereof. The compounds synthesized by the processes of the invention are useful for treating Alzheimer's disease and other diseases (e.g., cognitive impairment, schizophrenia, pain disorders, and sleep disorders) mediated by the muscarinic M1 receptor.

21 Claims, No Drawings

PROCESS FOR MAKING M1 RECEPTOR POSITIVE ALLOSTERIC MODULATORS

CROSS REFERENCE TO RELATED APPLICATIONS

This application is a U.S. National Phase application under 35 U.S.C. § 371 of PCT Application No. PCT/US2016/053652, filed Sep. 26, 2016, which claims priority under 35 U.S.C. § 119(e) from provisional Application No. 62/235,061, filed Sep. 30, 2015.

BACKGROUND OF THE INVENTION

Alzheimer's disease is a common neurodegenerative disease affecting the elderly, resulting in progressive memory impairment, loss of language and visuospatial skills, and behavior deficits. Characteristics of the disease include degeneration of cholinergic neurons in the cerebral cortex, hippocampus, basal forebrain, and other regions of the brain, neurofibrillary tangles, and accumulation of the amyloid β peptide (Aβ). Aβ is a 39-43 amino acid produced in the brain by processing of the beta-amyloid precursor protein (APP) by the beta-amyloid protein cleaving enzyme ("beta secretase" or "BACE") and gamma-secretase. The processing leads to accumulation of Aβ in the brain.

Cholinergic neurotransmission involves the binding of acetylcholine either to the nicotinic acetylcholine receptor (nAChR) or to the muscarinic acetylcholine receptor (mAChR). It has been hypothesized that cholinergic hypofunction contributes to the cognitive deficits of patients suffering from Alzheimer's Disease. Consequently, pharmacotherapeutic targets which increase the activation of muscarinic receptors to counteract cholinergic hypofunction have been explored. Muscarinic receptors are prevalent throughout the body. Five distinct muscarinic receptors (M1-M5) have been identified in mammals. In the central nervous system, muscarinic receptors are involved in cognitive, behavior, sensory, motor and autonomic functions. The muscarinic M1 receptor, which is prevalent in the cerebral cortex, hippocampus and striatum, has been found to have a major role in cognitive processing and is believed to have a role in the pathophysiology of Alzheimer's Disease. See Eglen et al, TRENDS in Pharmacological Sciences, 2001, 22:8, 409-414. Additionally, M1 agonists also have the potential to treat the underlying disease mechanism of Alzheimer's Disease. The cholinergic hypothesis of Alzheimer's Disease is linked to both β-amyloid and hyperphosphorylated tau protein. Formation of β-amyloid may impair the coupling of the muscarinic receptor with G-proteins. Stimulation of the M1 muscarinic receptor has been shown to increase formation of the neuroprotective αAPPs fragment, thereby preventing the formation of the Aβ peptide. Thus, M1 agonists may alter APP processing and enhance αAPPs secretion. See Fisher, Jpn J Pharmacol, 2000, 84:101-112.

Among the compounds thought to be useful for treating Alzheimer's disease are M1 receptor positive allosteric modulators of the kind illustrated in WO2010/059773, published May 27, 2010 and US2011-0224198, published Sep. 15, 2011, both of which are incorporated herein by reference in their entirety. Intermediates of the compounds disclosed herein are discussed in Tetrahedron Letters 44 (2003) 319-322. See also Journal of Biological Chemistry, vol. 289(48), 2014, pp 33701-33711. The present invention is directed to a novel process for synthesizing M1 receptor positive allosteric modulators which are substituted aryl methyl benzoquinazolinone compounds of the kind disclosed in WO2010/059773. The present invention is also directed to a novel process for synthesizing substituted aryl methyl benzoquinazolinone compounds under milder and more robust and predictable conditions. The compounds synthesized by the processes of the invention are useful for treating Alzheimer's disease and other diseases mediated by the muscarinic M1 receptor. Processes for making intermediates of the compounds disclosed herein can be found in WO2010/059773. See also Yu-Liang Yang et al., Tetrahedron Ltrs 44 (2003) 319-322.

SUMMARY OF THE INVENTION

The present invention is directed to a novel process for synthesizing substituted aryl methyl benzoquinazolinone compounds such as 3-[(1S,2S)-2-hydroxycyclohexyl]-6-[(6-methylpyridin-3-yl)methyl]benzo[h]-quinazolin-4(3H)-one, derivatives, and intermediates useful in the synthesis thereof under milder, more robust and predictable conditions to provide yields on a large scale. The compounds synthesized by the processes of the invention are useful for treating Alzheimer's disease and other diseases (e.g., cognitive impairment, schizophrenia, pain disorders, and sleep disorders) mediated by the muscarinic M1 receptor.

The following detailed descriptions are exemplary and are intended to provide further explanation of the invention claimed.

DETAILED DESCRIPTION OF THE INVENTION

The invention is directed to a method for synthesizing compounds of Formula I:

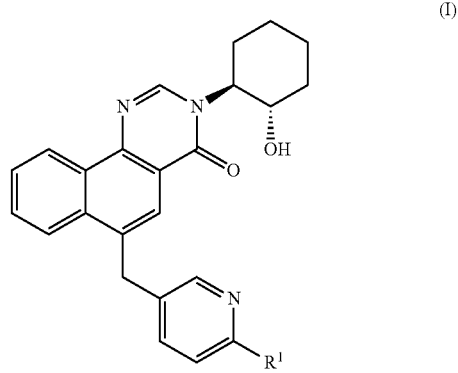

(I)

or a pharmaceutically acceptable salt thereof,
wherein $R^1$ is $C_{1-6}$ alkyl,
comprising introducing an alcohol protecting group (APG) onto a compound of Formula 8

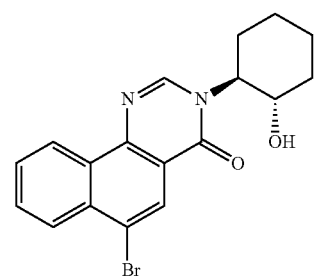

8 to make a compound of Formula 9:

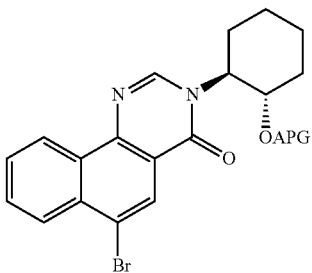

9 coupling the compound of Formula 9 with a compound of Formula 10

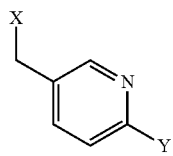

10 in the presence of a first palladium catalyst complex and optional first ligand in a first solvent to make a compound of Formula 11, wherein X is a metal-containing moiety and Y is a leaving group,

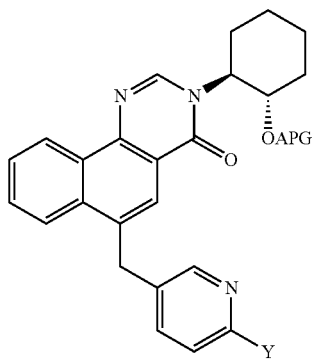

11 alkylating the compound of structural Formula 11 using an alkylating reagent to provide a compound of Formula 12:

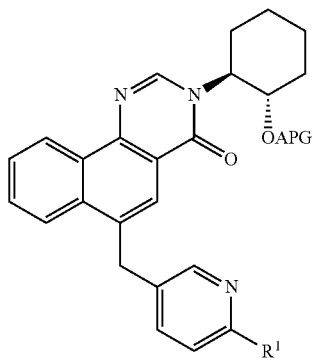

12 by way of step (1) or step (2) wherein:
step (1) comprises adding the alkylating reagent and optional inorganic base to the reaction mixture comprising the compound of Formula 11 without further isolation to make a compound of Formula 12, or
step (2) comprises isolating the compound of Formula 11 and reacting it with the alkylating reagent and optional inorganic base in the presence of the first palladium catalyst complex and optional first ligand, in a first solvent to provide a compound of Formula 12,
and deprotecting the alcohol protecting group in the compound of Formula 12 to yield a compound of Formula I.

In an embodiment, the metal-containing moiety, X, is selected from the group consisting of Li, MgCl, MgBr, MgI, ZnCl, ZnBr, ZnI, SnMe$_3$, Sn(n-Bu)$_3$, B(OH)$_2$, B(OR)$_2$, B(pinacol), B(N-methyliminoacetate), and BF$_3$K. An embodiment of this aspect of the invention is realized when X is ZnCl, ZnBr, or ZnI. Another embodiment of this aspect of the invention is realized when X is ZnCl.

In another embodiment, the process of making compound of formula I comprises contacting a compound of formula 8 with a borylating agent in the presence of a second palladium catalyst complex, optionally a second ligand, and an inorganic base in a first solvent to make a compound of Formula 9A:

9A

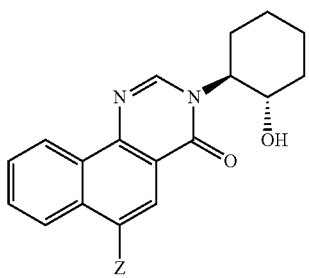

wherein Z is B(pinacol), or B(OH)$_2$,
coupling compound of Formula 9A with a compound of Formula 10A:

10A

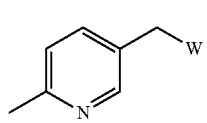

in the presence of a third palladium catalyst complex, optional third ligand and an inorganic base in a second solvent to produce a compound of Formula I, wherein W is OCOR$^W$, and R is C$_{1-6}$ alkyl, or C$_{1-4}$ haloalkyl. A subembodiment of this aspect of the invention is realized when R$^W$ is methyl.

An embodiment of the borylation step of this invention is realized when the borylating agent is a compound of Formula B or B':

B

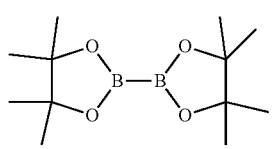

-continued

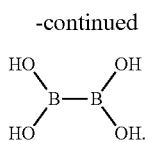

Another embodiment of the borylation step of this invention is realized when Z is B(pinacol). Still another embodiment of the borylation step of this invention is realized when Z is $B(OH)_2$. Yet another embodiment of the borylation step of this invention is realized when the resulting borylated solution contains a mixture of 9A with B(pinacol) and 9A with $B(OH)_2$ when B is used as the borylating agent. A subembodiment of this aspect of the invention is realized when the borylated mixture contains less than 5% of $B(OH)_2$ when B is used as a borylating agent. A subembodiment of this aspect of the invention is realized when the borylated mixture contains less than 3% of $B(OH)_2$ when B is used as a borylating agent. A subembodiment of this aspect of the invention is realized when the borylated mixture contains less than 1% of $B(OH)_2$ when B is used as a borylating agent.

In alternate reactions those skilled in the art of organic chemistry may also make 9A intermediates where Z is $BF_3K$, or B(N-methyliminoacetate) utilizing known procedures.

The term "alkyl," as used herein, refers to an aliphatic hydrocarbon group having one of its hydrogen atoms replaced with a bond having the specified number of carbon atoms. For example, in different embodiments, an alkyl group contains from 1 to 6 carbon atoms ($C_1$-$C_6$ alkyl) or from 1 to 3 carbon atoms ($C_1$-$C_3$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. In one embodiment, an alkyl group is linear. In another embodiment, an alkyl group is branched.

The term "haloalkyl," as used herein, refers to an alkyl group as defined above, wherein one or more of the alkyl group's hydrogen atoms has been replaced with a halo. In one embodiment, a haloalkyl group has from 1 to 6 carbon atoms. In another embodiment, a haloalkyl group has from 1 to 3 carbon atoms. In another embodiment, a haloalkyl group is substituted with from 1 to 3 halo atoms. Non-limiting examples of haloalkyl groups include —$CH_2F$, —$CHF_2$, and —$CF_3$. The term "$C_1$-$C_4$ haloalkyl" refers to a haloalkyl group having from 1 to 4 carbon atoms.

The term "aryl," as used herein, refers to an aromatic monocyclic or multicyclic ring system comprising from about 6 to about 14 carbon atoms. In one embodiment, an aryl group contains from about 6 to 10 carbon atoms ($C_6$-$C_{10}$ aryl). In another embodiment an aryl group is phenyl. Non-limiting examples of aryl groups include phenyl and naphthyl.

The term "alcohol protecting group" (APG), also referred to as "oxygen protecting group" means a substituent that protects an oxygen group in a reaction from a reagent or chemical environment. Alcohol protecting groups are well known in the art and include for example silyl, acyl, and pyranyl protecting groups such as tert-butyldimethylsilyl (TBS), trimethylsilyl (TMS), acetyl (Ac), tetrahydropyranyl (THP), and the like. Methods for protecting and deprotecting an alcohol group are also well within one having ordinary skill in the art. In another embodiment, the invention encompasses the process described herein wherein APG is TBS, TMS, or Ac. Still in another embodiment, the invention encompasses the process described herein wherein APG is TBS. When APG is TBS, TMS, or acetyl, reagents that can be used to install APG includes TBSCl, TBSOTf, TBS-imidazole, TBS-CN, TMSCl, TMSOTf, TMS-imidazole, TMSCN, AcCl, $Ac_2O$ and the like.

The term "leaving group" means an atom or atom group that leaves from a substrate in a substitution or elimination reaction and includes for example halogen and sulfonate. In an embodiment, the invention encompasses the process described herein wherein the leaving group Y is selected from the group consisting of: halogen, $OSO_2R^\wedge$ ($R^\wedge$=alkyl, fluoroalkyl, and aryl) OMs (mesylate), OTs (tosylate), OBs (besylate), $OSO_2CF_3$ (OTf), $OSO_2CF_2CF_2CF_3$, OP(O)($OR^i$)$_4$, $OC(O)R^i$, $OC(O)OR^i$ and $OC(O)NR^iR^{ii}$, wherein $R^i$ and $R^{ii}$ are independently selected from H and $C_{1-6}$alkyl including fluorinated alkyls such as $CF_3$ or $CF_3CF_2CF_2CF_2$). In another embodiment, the invention encompasses the process described herein wherein Y is halogen such as chloro, bromo, fluoro, or iodo.

Suitable first and second solvents include for example water, methanol (MeOH), ethanol (EtOH), isopropyl alcohol (iPrOH), t-Butyl alcohol (tBuOH), t-Amyl alcohol (t-AmOH), tert-butyl methyl ether (MTBE), tetrahydrofuran (THF), 2-methyltetrahydrofuran (2-MeTHF), ethyl acetate (EtOAc), isopropyl acetate (iPrOAc), acetone, dimethylformamide (DMF), acetonitrile (MeCN), toluene, ethylene glycol, chlorobenzene, 1,4-dioxane, dichloromethane ($CH_2Cl_2$), 1,2-dichloroethane, CPME (cyclopentyl methyl ether), 1,2-dimethoxyethane (DME), dimethylsulfoxide (DMSO), dimethylacetomide (DMAc), N-methylpyrrolidinone (NMP), and 1,3-Dimethyl-3,4,5,6-tetrahydro-2(1H)-pyrimidinone (DMPU). In the boroylation step water is not a suitable first solvent.

Suitable inorganic bases include for example KOAc, $K_2CO_3$, $K_3PO_4$, KF, $Cs_2CO_3$, KOH, NaOH, LiOH, DIPEA, $KHCO_3$, and $NaHCO_3$. Particular inorganic bases include KOAc, $K_3PO_4$, and $K_2CO_3$.

In another embodiment, the invention encompasses the process described herein wherein the first solvent selected from the group consisting of THF, 2-MeTHF, EtOAc, iPrOAc, ethylene glycol, CPME, MeCN, DMF, toluene, 1,4-dioxane, chlorobenzene, MTBE, $CH_2Cl_2$, DME, DMSO, DMAc, and NMP. In another embodiment, the invention encompasses the process described herein wherein the first solvent is THF or DMF.

In another embodiment, the invention encompasses the process described herein wherein the second solvent is selected from the group consisting of THF, water, 2-MeTHF, EtOAc, MeOH, EtOH, iPrOH, tBuOH, t-AmOH, iPrOAc, MTBE, CPME, DMAc, 1,4-dioxane, $CH_2Cl_2$, DME, DMF, DMSO, toluene, chlorobenzene, 1,2-dichloroethane, MeCN, ethylene glycole, and NMP. In another embodiment, the invention encompasses the process described herein wherein the second solvent is iPrOH, THF, water or a combination thereof.

Suitable alkylating reagents useful in the instant invention include MeZnCl, $Me_2Zn$, $MeB(OH)_2$, $MeMgCl/ZnCl_2$, $MeLi/ZnCl_2$, and $SnMe_4$. In another embodiment, the invention encompasses the process described herein wherein the alkylating reagent is MeZnCl.

The palladium catalyst complex (which is already coupled with a ligand) can be added alone or with another ligand to facilitate the reaction. Suitable first, second and third palladium catalyst complexes useful in the instant invention include PCy3-G2-palladacycle (Chloro[(tricyclohexylphosphine)-2-(2'-aminobiphenyl)]palladium(II)), $(Pd(tBu_3P)_2$, $Pd_2dba_3$-$CHCl_3$, $Pd(OAc)_2$, $Pd(dba)_2$, $Pd(TFA)_2$, Pd(MeCN)$_2$Cl$_2$, Pd(allyl)Cl dimer, Pd(cinnamyl)Cl dimer (Bis[cinnamyl palladium(II) chloride]), Pd(aminobiphenyl)Cl dimer ((2'-amino-[1,1'-biphenyl]-2-yl)palladium(II) chloride dimer), or Pd(aminobiphenyl)OMs dimer ((2'-amino-[1,1'-biphenyl]-2-yl)palladium(II) methanesulfonate). In an embodiment, the invention encompasses the process described herein wherein the first palladium catalyst complex is Pd(tBu$_3$P)$_2$. In an embodiment, the invention encompasses the process described herein wherein the first palladium catalyst complex is Pd$_2$dba$_3$, or Pd$_2$dba$_3$-CHCl$_3$. In an embodiment, the invention encompasses the process described herein wherein the first palladium catalyst complex is Pd(OAc)$_2$. In an embodiment, the invention encompasses the process described herein wherein the second palladium catalyst complex is PCy3-G2-palladacycle. In an embodiment, the invention encompasses the process described herein wherein the third palladium catalyst complex is Pd(OAc)$_2$.

Suitable ligands useful in the instant invention include organophosphorus compounds such as XPhos, SPhos, JohnPhos, DavePhos, RuPhos, tetramethyl tBuXPhos, BrettPhos, CataCXium A, QPhos, tributylphosphonium tetrafluoroborate (t-Bu$_3$P-HBF$_4$), 1,4-bis(diisopropylphosphanyl)butane, and bis(diphenylphosphanyl)ferrocene, Amphos, dtbpf, dppf, dippf, bis(diphenylphosphino)propane (dppp), bis(diphenylphosphino)butane (dppb), DPEhos, Xantphos, bis(diphenylphosphino)-1,1'-binaphthyl (BINAP), SL-J009-1 ((R)-1-[(S)-2-(Dicyclohexylphosphino)ferrocenyl]-ethyldi-tert.-butylphosphine), SL-J009-2 ((S)-1-[(R)-2-(Dicyclohexylphosphino)ferrocenyl]-ethyldi-tert.-butylphosphine), CataCXium PtB, tBuXPhos, PCy3, Cy3P-HBF4, and tri-o-tolyl phosphine In an embodiment, the invention encompasses the process described herein wherein second palladium catalyst complex is PCy3-G2-palladacycle. Still in another embodiment, the invention encompasses the process described herein wherein the third palladium catalyst complex is Pd(OAc)$_2$, which is accompanied with a third ligand. A subembodiment of this aspect of the invention is realized when the third ligand is RuPhos.

In an embodiment, the invention encompasses the process described herein wherein the hydroxyl group in the compound of Formula 8 is protected to make a compound of Formula 9 by reacting the compound of Formula 8 with a alcohol protecting group, previously described, in the presence of a first base selected from the group consisting of imidazole, NEt$_3$, DIPEA, NaOtBu, DMAP, pyridine, 2,6-lutidine, N-methylmorpholine, and Cy$_2$NMe and first solvent to make a compound of Formula 9. A particular base is imidazole and first solvent is DMF. In a subembodiment of this aspect of the invention the alcohol protecting group is selected from the group consisting of TBS, Ac, and TMS. A particular alcohol protecting group is TBS.

In an embodiment, the invention encompasses the process described herein wherein compound of Formulas 9 and Formula 10 are coupled in the presence of the first palladium-ligand complex in the first solvent at a temperature range of −20° C. to about 100° C. to make a compound of Formula 11. In still a further embodiment, the reaction of coupling the compound of Formulas 9 and 10 is conducted at a temperature range of 0° C. to about 25° C. In a subembodiment of this aspect of the invention the first palladium-ligand complex is Pd(tBu$_3$P)$_2$ or Pd$_2$dba$_3$. In yet another subembodiment of this aspect of the invention is realized when the first solvent is THF.

In an embodiment, the invention encompasses the process described herein wherein the compound of Formula 12 is made from the compound of Formula 11 by step (1) wherein the alkylating agent and optional inorganic base is added to the mixture containing the compound of Formula 11 without isolation. In a subembodiment of this aspect of the invention an inorganic base is not used. In another subembodiment, the inorganic base is potassium phosphate. In another subembodiment, a particular alkylating agent is MeZnCl. An embodiment of step (1) of the invention is realized wherein when X was a boron containing moiety an exogenous base (K$_2$CO$_3$, K$_3$PO$_4$, KF, Cs$_2$CO$_3$, KOH, NaOH, LiOH, DIPEA, KHCO$_3$, and NaHCO$_3$.) is added. Another embodiment of step (1) is realized wherein when X was Li, MgCl, MgBr, or MgI a zinc salt may optionally be added (ZnCl$_2$, ZnBr$_2$, ZnI$_2$).

In a further embodiment, the reaction of step (1) is conducted at a temperature range of −20° C. to about 100° C. In still a further embodiment, the reaction of step (1) is conducted at a temperature range of 5° C. to about 25° C.

In an embodiment, the invention encompasses the process described herein wherein the compound of Formula 12 is made from the compound of Formula 11 by step (2) wherein the compound of Formula 11 is isolated and reacted with the alkylating reagent in the presence of the first palladium-ligand complex and optional inorganic base. In another embodiment of this aspect of the invention, the inorganic base is potassium phosphate, the first palladium-ligand complex is Pd(tBu3P)2 and the alkylating agent is MeZnCl. A particular inorganic base is K$_3$PO$_4$. In a subembodiment of this aspect of the invention an inorganic base is not used. In a further embodiment of this aspect of the invention, the reaction of step (2) is conducted at a temperature range of −20° C. to about 100° C. In still a further embodiment, the reaction of step (2) is conducted at a temperature range of 5° C. to about 25° C.

In an embodiment, the invention encompasses the process described herein wherein the compound of Formula 12 is deprotected by reaction with an acid in the presence of a third solvent to make a compound of Formula I. An aspect of this embodiment is realized when the acid is selected from the group consisting of HCl, H$_2$SO$_4$, HOAc, TFA, HBr, MsOH, p-TsOH, HBF$_4$, HF-pyr, HF-MeCN, HF-NEt$_3$, KHF$_2$, TBAF (tetra-n-butylammonium fluoride), and TMAF (tetramethylammonium fluoride). Another aspect of this embodiment is realized when the acid is HCl. Still another aspect of this embodiment is realized when the third solvent is THF, water, or a combination thereof.

In an embodiment, the invention encompasses a process wherein compound 8 undergoes a borylation to make the compound of 9A where Z is B(pinacol), using Bis(pinacolato)diboron as the borylation agent, PCy3-G2-palladacycle as a second palladium catalyst complex, PCy3 as a ligand, KOAc as the inorganic base, and THF as the first solvent. In an embodiment, the invention encompasses a process wherein compound 8 is borylated to make the compound of 9A where Z is B(OH)$_2$, using B$_2$(OH)$_4$ as the borylation agent, PCy3-G2-palladacycle as a second palladium catalyst complex, KOAc as the inorganic base, and THF as the first solvent. In a further embodiment of this aspect of the invention, the borylation step is conducted at a temperature range of −20° C. to about 80° C. In still a further embodiment, the borylation step is conducted at a temperature range of 25° C. to about 80° C. A particular temperature range is 50° C. to about 70° C.

In an embodiment, the invention encompasses the process described herein wherein compound 9A is coupled with compound 10A in the presence of a third palladium catalyst complex that is Pd(OAc)$_2$, a third ligand that is RuPhos, and an inorganic base that is K$_2$CO$_3$ in a second solvent that is IPA, water, or a combination thereof to produce a compound of Formula I. In a further embodiment of this aspect of the invention, the coupling of compounds 9A and 10A is conducted at a temperature range of −20° C. to about 100° C. In still a further embodiment, the borylation step is conducted at a temperature range of 50° C. to about 90° C. A particular temperature range is 70° C. to about 90° C.

The compound of Formula I may be synthesized as described in WO 2010/059773, or in commonly owned, co-pending application under (U.S. Patent Publication 20180273507) filed contemporaneously with this application. In an alternate embodiment the present invention provides a novel synthesis of crystalline salt forms of Compound I, e.g. free base, form 1, or butenedioate, form 1. A non-limiting example of this synthesis may be described by the description that follows. Reactants for which a synthesis is not described are available commercially for purchase. An aspect of this embodiment is realized when the compound of Formula I, optionally in the presence of a solvent, is contacted with a suitable acid such as acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methansulfonic, mucic, nitric, pamoic, pantothenic, phosphoric, succinic, sulfuric, tartaric, p-toluenesulfonic acid, and the like. In one embodiment the salt is fumarate, or butenedioate of the compound of Formula I. Still another embodiment of this aspect of the invention is realized when the solvent includes water and/or a suitable organic solvent. Non-limiting examples of organic solvents include EtOH, MeOH, iPrOH, $CH_2Cl_2$, THF, 2-MeTHF, MTBE, DME (1,2-dimethoxyethane), 1,4-dioxane, CPME (cyclopentyl methyl ether), EtOAc, iPrOAc, tBuOH, t-AmOH, toluene, DMF, DMAc, NMP, and DMSO. In one such embodiment, the organic solvent is EtOH. In a further embodiment of this aspect of the invention, the crystalline salt forming step is conducted at a temperature of about 25° C. to about 85° C. In still a further embodiment, the crystalline salt forming step is conducted by contacting the compound of Formula I with a suitable acid in the presence of an organic solvent at a temperature of about 30° C. to about 75° C., adding crystalline butenedioate Compound I, form I solution as seed and aging the solution for up to 48 hours. In another embodiment, the crystalline salt forming step is conducted by adding over 1 to 24 hours additional acid solution at a temperature of about 25° C. to about 85° C. In yet another embodiment, the crystalline salt forming step is conducted at a temperature of about 40° C. to about 60° C., preferably 45° C. to about 55° C., more preferably 50° C. for 2 to 24 hours. In another embodiment, the crystalline salt forming step is conducted at a temperature of about 45° C. to about 55° C., cooled to about −20° C. to 15° C. over 2 to 12 hours and aged at −20° C. to 15° C. for up to 24 hours. In still another embodiment, the crystalline salt forming step is conducted at a temperature of about 50° C., cooled to about 0° to about 5° C. at a rate of about 2° C. to about 7° C. per hour and aged at about 0° to about 5° C. for up to 24 hours. In yet another embodiment, the crystalline salt forming step is conducted at a temperature of about 50° C., cooled to about 0° to about 5° C. at a rate of about 5° C. per hour and aged at about 0° to about 5° C. for up to 24 hours. The solution can then be filtered and the resultant crystals collected. Alternatively, the resultant crystals can be milled at a temperature of about −10° C. to about 15° C., heated to a temperature of about 25° C. to about 85, preferably about 45° C. to about 55 and then cooled to room temperature before filtration and collection of the crystals The process of the present invention offers greater efficiency, reduced waste, and lower cost of goods relative to the methods for making the subject compounds existing at the time of the invention. Particularly, for the process employing structure 10A, the MeZnCl stage of the reaction has been replaced by a borylation step. From a cost and robustness perspective, this is a favorable exchange. Robustness is also addressed by using intermediates such as protected alcohol 9.

The following examples illustrate the invention. Unless specifically indicated otherwise, all reactants were either commercially available or can be made following procedures known in the art.

Intermediates needed to make compound of Formula 8 can be obtained from commercial sources, and/or by methods disclosed in U.S. Pat. No. 8,557,832 (U.S. Ser. No. 13/129,593), incorporated herein in its entirety. The compound of Formula 8 also can be made as depicted in Example 1:

Example 1

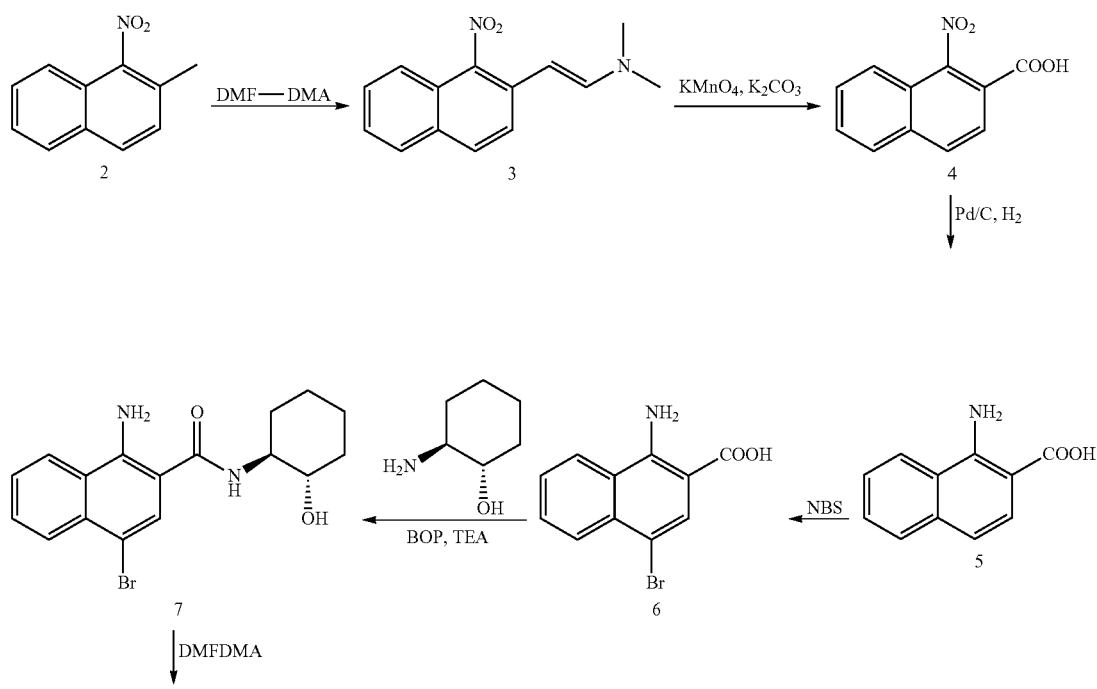

-continued

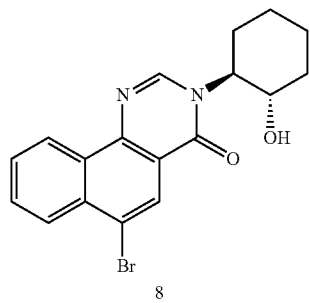
8

Step 1:

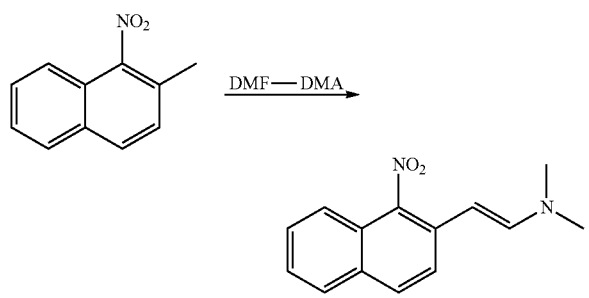

Compound 2 (17.9 g) and DMF-DMA (59.4 g) was dissolved in DMF (190 mL) and degassed. The mixture was heated to 125-135° C. for 24 hours. The mixture was concentrated to ~40 mL total volume under vacuum and cooled to 10-15° C. Water (234 mL) was added to crystallize compound 3. Compound 3 was then isolated by filtration, washed with water (61 mL), and dried to give 22.2 g of 3 in 93.0% yield, 99.1 LCAP, and 96.9 wt %.

Step 2:

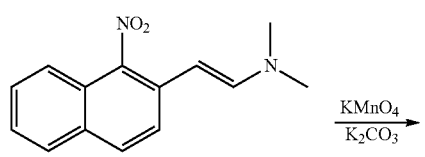

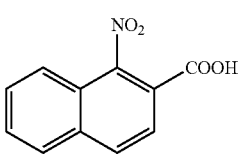

Compound 3 (22.2 g) was dissolved in THF (367 mL) and added to a cold (0-20° C.) mixture of $K_2CO_3$ (26.1 kg), $KMnO_4$ (87.05 g) in water (320 mL). The mixture was warmed to rt and aged at rt for 2 hours. The mixture was filtered and the cake was washed with a mixture of THF (64.1 mL) and water (46.2 mL). The filtrate was concentrated under vacuum to a total volume of approximately 600 mL to remove the THF. The pH of the water solution was then adjusted to 7-8 using 7.8 g of 18 wt % aqueous HCl. The mixture was filtered and washed with water (10 mL). The filtrate was acidified to pH 1-2 using 121 g of 18 wt % aqueous HCl at 10-15° C. The slurry was then aged at 0-5° C. for 6 hours. The product was then isolated by filtration, washed with water (66 mL), and dried to give 17.3 g of compound 4 in 86.0% yield, 98.9 LCAP, and 95.9 wt %.

Step 3:

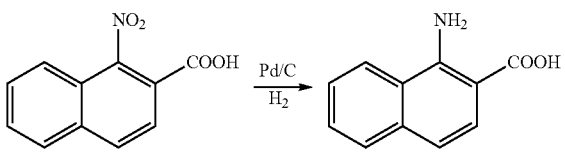

Compound 4 (17.3 g), acetic acid (2 g), Pd/C (1.83 g, 10 wt % Pd) were suspended in THF (339 mL) at rt. The mixture was degassed and pressurized with hydrogen (25 psig). The mixture was aged for 10 hours, filtered over diatomite (6 g) and washed with THF (51 mL). The filtrate was concentrated to approximately 40 mL total volume and cooled to 0-5° C. Water (143 mL) was added to crystallize the product. Compound 5 was then isolated by filtration, washed with water (100 mL), and dried to give 13.35 g of compound 5 in 92.2% yield, 99.5 LCAP, and 98.7 wt %.

Step 4:

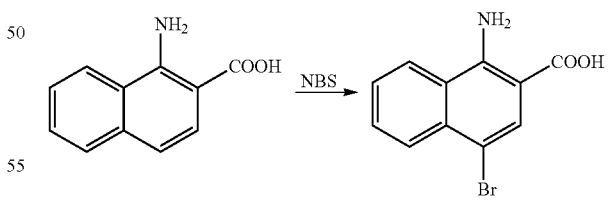

A solution of NBS (12.9 g) in DMF (28 mL) was added slowly to a mixture of compound 5 (13.35 g) and THF (89 mL) at 0-5° C. The mixture was warmed to rt and water (121 mL) was added. The mixture was concentrated to a total volume of approximately 120 mL, and cooled to 10-15° C. The mixture was aged for 1 h. Compound 6 was then isolated by filtration, washed with water (53 mL), and dried to give 18.05 g compound 6 in 95% yield, 99.6 LCAP, and 98.1 wt %.

Step 5:

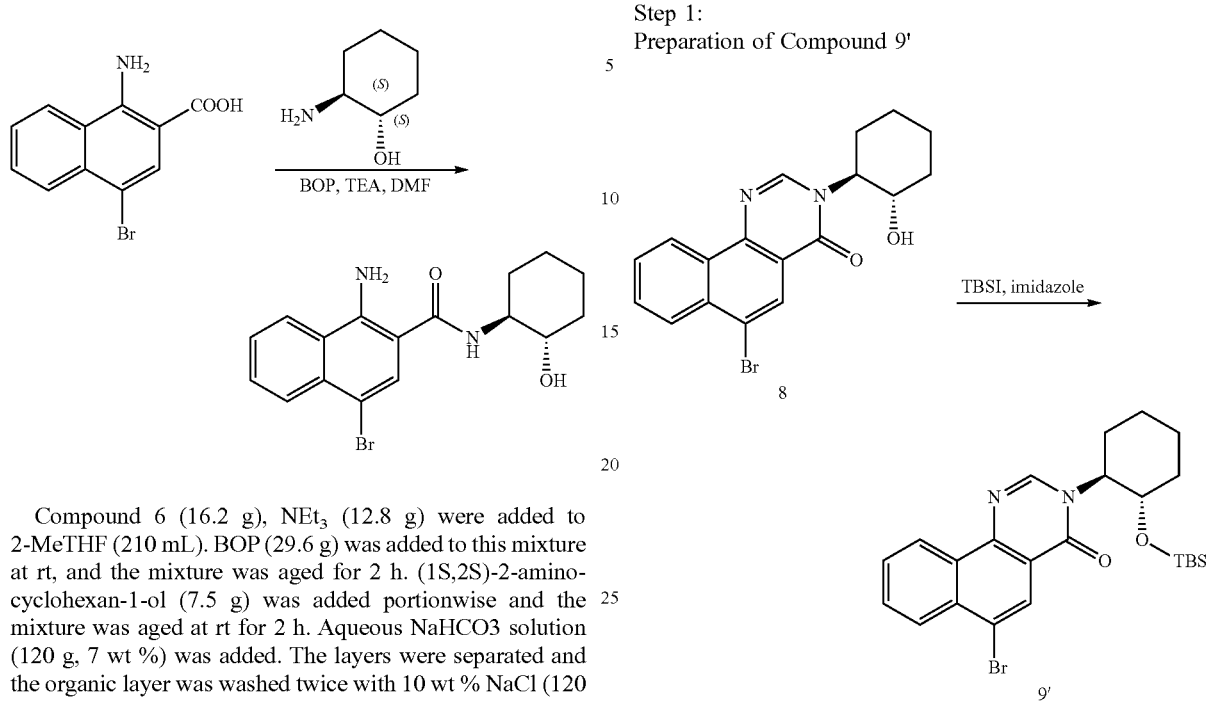

Compound 6 (16.2 g), NEt₃ (12.8 g) were added to 2-MeTHF (210 mL). BOP (29.6 g) was added to this mixture at rt, and the mixture was aged for 2 h. (1S,2S)-2-amino-cyclohexan-1-ol (7.5 g) was added portionwise and the mixture was aged at rt for 2 h. Aqueous NaHCO3 solution (120 g, 7 wt %) was added. The layers were separated and the organic layer was washed twice with 10 wt % NaCl (120 g). The 2-MeTHF in the organic layer was replaced by MeCN (80 mL) via vacuum distillation. The slurry was filtered, washed with MeCN (22 mL), and dried to give 20.85 g of compound 7 in 94.2% yield, 99.8 LCAP, and 98.6 wt %.

Step 6:

Compound 7 (20.85 g) and DMF-DMA (93.8 g) were added to DMF (40.5 mL). The mixture was degassed and heated to 70-80° C. for 2 h. The mixture was concentrated to approximately 50 mL and cooled to rt. Water (161 mL) was added and the mixture was aged at 5-10° C. for 2 h. The product was isolated by filtration, washed with water (2×48.5 mL), and dried to give 20.35 g of compound 8 in 94.2% yield, 99.7 LCAP, and 99.2 wt %.

Example 2

Step 1:
Preparation of Compound 9'

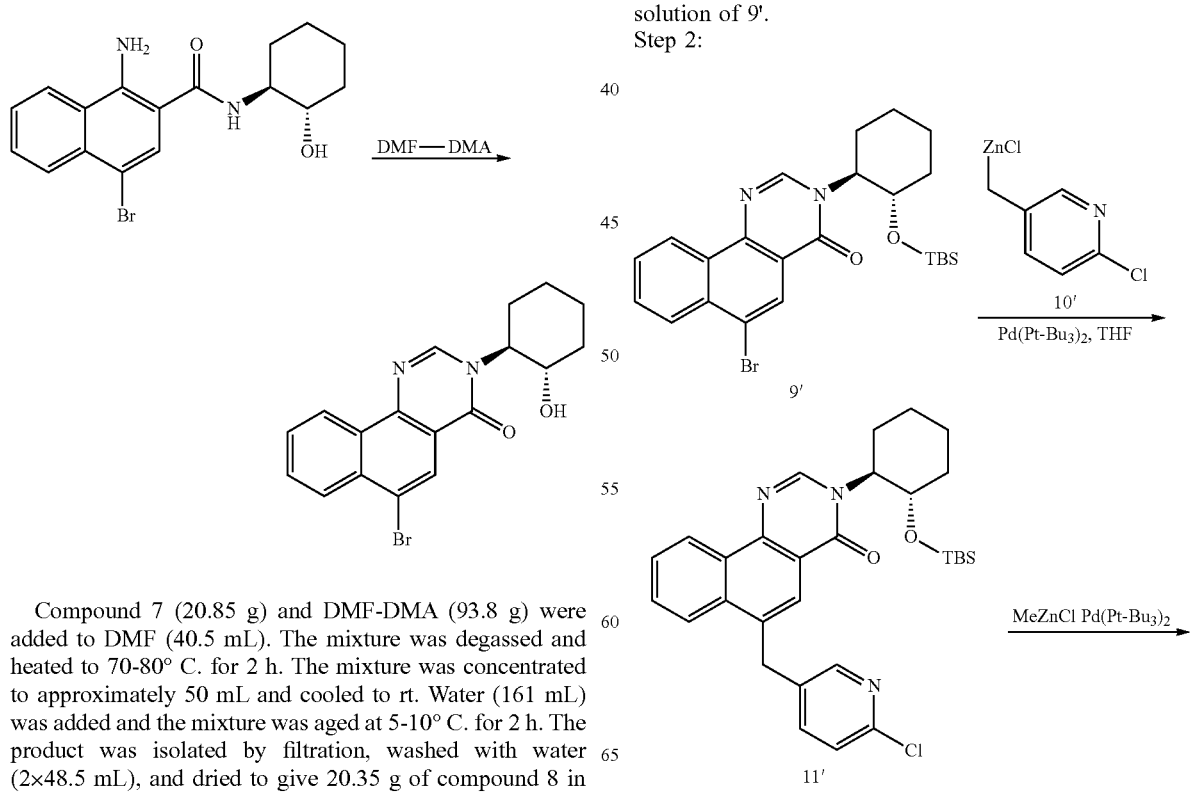

Compound 8 (18.0 g), imidazole (6.8 g), and TBSCl (10.4 g) were dissolved in DMF (37 mL). The mixture was aged at room temperature for 2-3 hours and diluted with MTBE (175 mL) and water (96 mL). The layers were separated and the organic layer was washed with water (94 mL). The MTBE was replaced by THF via distillation to give a THF solution of 9'.

Step 2:

15
-continued

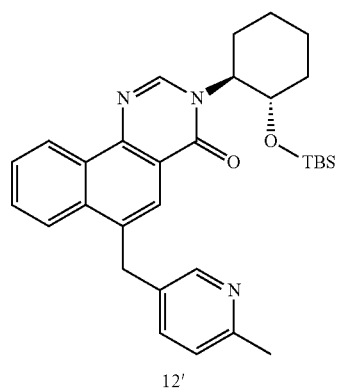

12'

16
-continued

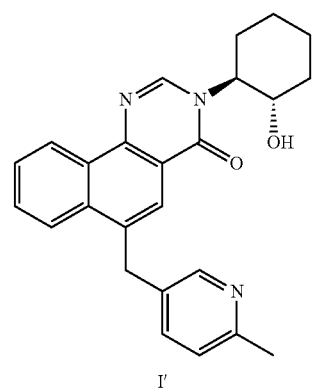

I'

THF solution of 9' from previous step was azeotropically distilled with THF and then cooled to 5-10° C. A 11.9 wt % solution of 10' in THF (73 g total solution weight) was added. The mixture was degassed and Pd(PtBu$_3$)$_2$ catalyst was added. The mixture was stirred for 4 hours at 5-15° C., and 26.2 g of a 23.1 wt % solution of MeZnCl in THF was added at 5-15° C. The mixture was aged at 5-15° C. for 9 hours. The reaction mixture was diluted with 318 g of aqueous disodium EDTA/NaHCO$_3$ solution (15 wt % disodium EDTA, 9.7 wt % NaHCO$_3$) and MTBE (175 mL). The layers were separated and the organic layer was successively washed with another 292 g of the aqueous disodium EDTA/NaHCO$_3$ solution, 90 mL of water, and 4×80 g of aqueous 2-mercaptobenzoic acid solution (0.19 wt % 2-mercaptobenzoic acid, 0.41 wt % NaHCO$_3$), 80 mL water, and 85 g of 25 wt % aqueous NaCl solution. The organic layer was treated with 1.8 g of MP-TMT and 3.6 g of Ecosorb C941 and filtered. Product 12' was crystallized from n-heptane (~80 mL) to give 15 g in 83.9% yield, 98.1 wt %, and 99.2 LCAP.

$^1$H NMR of 12': 9.04 (1H, m), 8.48 (1H, d, J=2.4 Hz), 8.18 (1H, s), 8.08 (1H, s), 7.98 (1H, m), 7.66 (2H, m), 7.30 (1H, dd, J=7.6, 2.4 Hz), 7.00 (1H, d, J=8 Hz), 4.46 (2H, s), 4.33 (1H, br s), 2.5 (3H, s), 2.14-1.89 (6H, br), 1.44 (3H, br m), 0.63 (9H, s), −0.03 (3H, s), −0.34 (3H, s)

Step 3:

Compound 12' (15 g) was dissolved in THF (14.1 mL), water (16 mL), and concentrated hydrochloric acid (7.5 mL). The mixture was aged at 25-30° C. for 12 hours and diluted with water (158 mL) and dichloromethane (158 mL). NaHCO$_3$ (10.5 g) was added to the mixture. The layers were separated and the organic layer was washed twice with water (80 mL each time). Compound I' was then isolated by crystallization from a mixture of toluene and n-heptane to give 10.8 g in 91.6% yield.

$^1$H NMR of I': NMR spectra consistent with theory and a mass ion (ES+) of 400.0 for [M+H]$^+$: $^1$H NMR (400 MHz, CDCl$_3$) δ 9.00-8.99 (m, 1H), 8.45 (s, 1H), 8.29 (s, 1H), 7.95 (s, 1H), 7.95-7.76 (m, 1H), 7.68-7.63 (m, 2H), 7.27-7.17 (m, 1H), 6.96 (d, J=8.0 Hz, 1H), 4.62 (br s, 1H), 4.35 (s, 2H), 4.11 (br s, 1H), 2.48 (s, 3H), 2.29-2.20 (m, 1H), 1.95-1.90 (m, 3H), 1.65-1.39 (m, 5H).

Example 3

Step 1: Preparation of 9A"

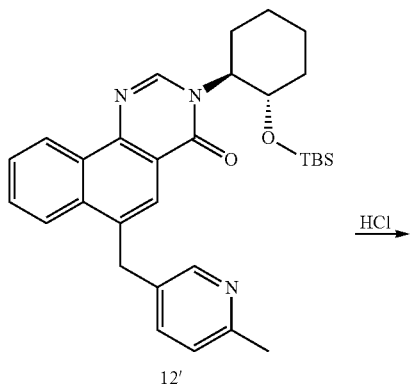

12'

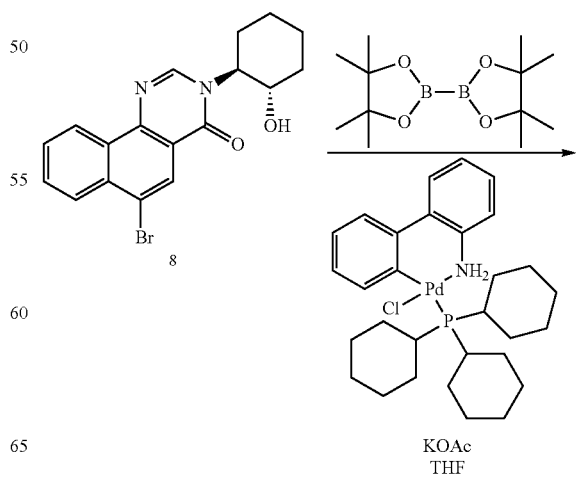

KOAc
THF

17
-continued

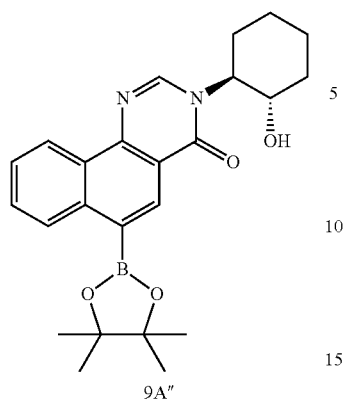

9A″

Compound 8 (33.0 g), bis(pinacolato)diboron (23.3 g) and potassium acetate (25.8 g) were suspended in THF (330 mL). The TCP-G2-Palladacycle (517 mg) in THF (1.12 mL) was added to the reaction mixture and de-gassed. The mixture was heated to 67° C. for 23 h. The reaction mixture was cooled to 25° C. EtOAc (165 mL) was added, followed by water (83 mL). The layers were separated and the organic layer was washed with water (83 mL). The product 9A″ was then crystallized from a mixture of MeCN (~200 mL) and water (187 mL) to give 32.64 g of product in 89% isolated yield, 100 wt %, and 99.6 LCAP, after filtration and washing the wet cake with a mixture of MeCN (34 mL) and water (34 mL).

Step 2:

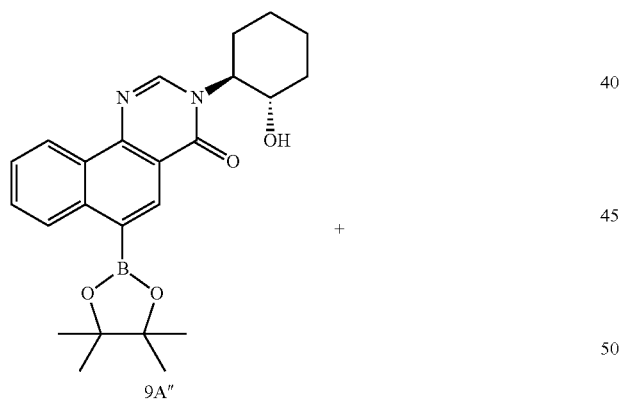

9A″

+

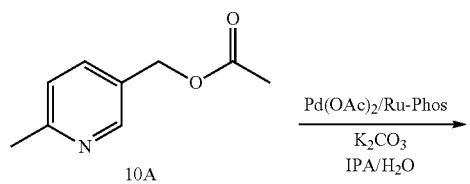

10A

Pd(OAc)₂/Ru-Phos
K₂CO₃
IPA/H₂O

18
-continued

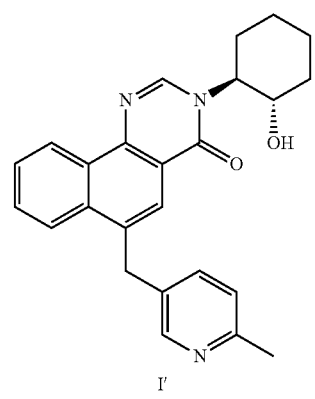

I′

Pinacol boronate 9A (30.0 g), palladium acetate (80.8 mg) and Ru-Phos (331 mg) were charged to a reaction flask followed by a solution of commercially available pyridine acetate 10A (14.2 g) in IPA (47.1 mL). IPA (300.6 mL), water (30 mL), and potassium carbonate (29.6 g) were then added. The reaction mixture was sparged sub-surface with nitrogen for 5 minutes. The reaction was heated to 82° C. for 1 h. The reaction was cooled to 21° C. then diluted with water (75 mL) and MTBE (75.5 mL). The layers were separated and the organic layer was washed successively with 25 wt % NaCl aqueous solution (100 g) and 25 weight (wt) % ammonium chloride aqueous solution (100 g). The organic layer was then diluted with MTBE (75.5 mL) and water (75 mL). The layers were separated and the organic layer was filtered and concentrated to 37.5 mL, and MP-TMT resin (4.5 g), IPA (25.4 mL), and MTBE (5.4 mL) were added to the filtrate. The mixture was aged for 10 h, filtered and the product was crystallized from a mixture of toluene (~90 mL) and heptane (440 mL) to give 26.2 g in 92% isolated yield, >99 wt %, >99 LCAP after filtration and washing with a mixture of toluene (20 mL) and heptane (50 mL).

Example 4

Formula I

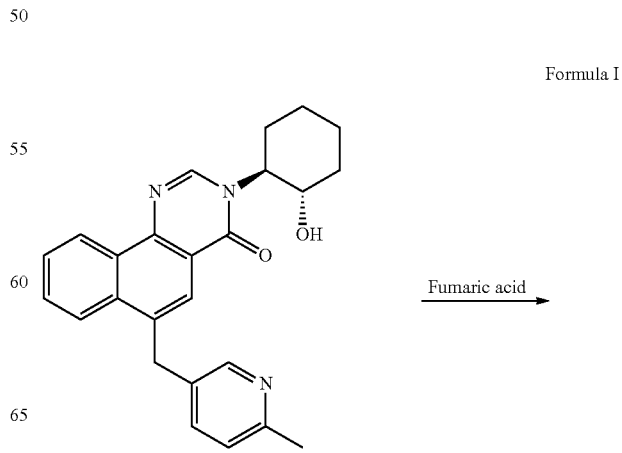

Fumaric acid →

-continued

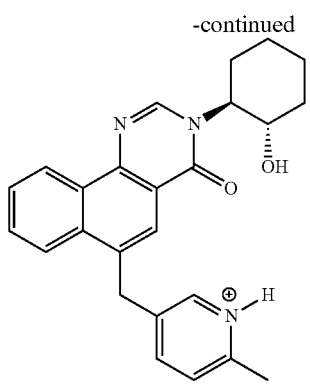

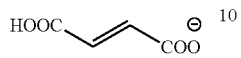

Crystalline Butenedioate of Compound I, form 1

18.0 g of the compound Formula I free base was dissolved in EtOH (270 mL) at 50° C. and filtered. In a separate vessel, fumaric acid (0.94 g) was dissolved in EtOH (32 mL) at 50° C. The fumaric acid solution was charged to the solution of via an in-line filter. The mixture was seeded with crystalline butenedioate of Compound I, form 1 (0.3 g) and the mixture was aged at 50° C. for 12 h.

In another vessel, additional fumaric acid (4.29 g) was dissolved in EtOH (130 mL) at 50° C. and then added to the above solution of Formula I free base and fumaric acid at 50° C. over 12 h. The combined batch was then cooled to 0° C. over 6 h and aged at 0 C for 4 h. The batch was then wet milled at 23-35 m/s tip speed for 2 hours. The milled batch was then heated to 50° C. for 1 h, then cooled to 0° C. over 3 h and aged at 0° C. for an additional 1 h. The batch was then filtered and washed with EtOH (52 L) to provide 20.57 g of crystalline butenedioate of Compound I, form 1 in 89% yield.

$^1$H NMR (d6-DMSO): 8.98 (1H, dd, J=7.6, 1.9 Hz), 8.64 (1H, br s), 8.44 (1H, d, J=2.0 Hz), 8.16 (1H, dd, J=7.2, 1.5 Hz), 7.93 (1H, s), 7.75 (2H, m) 7.47 (1H, dd, J=8.0, 2.3 Hz), 7.13 (1H, d, J=8.0 Hz), 6.63 (2H, s), 4.49 (3H), 4.03 (1H, br s), 2.40 (3H, s), 2.03 (1H, br s), 1.87-1.71 (4H, br m), 1.36 (3H, br m).

What is claimed is:

1. A process for the preparation of a compound of formula I:

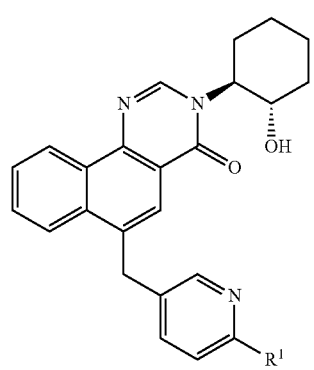
(I)

or a pharmaceutically acceptable salt thereof,
wherein R$^1$ is C$_{1-6}$ alkyl, or C$_{6-10}$ aryl
comprising introducing an alcohol protecting group (APG) onto a compound of Formula 8

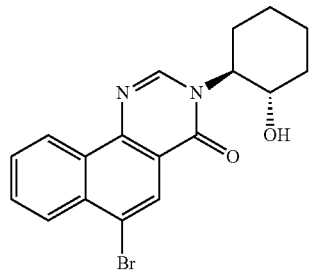
8 to make a compound of Formula 9:

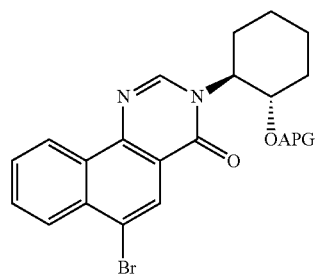
9 coupling the compound of Formula 9 with a compound of Formula 10

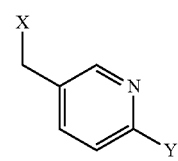
10 in the presence of a first palladium catalyst complex to make a compound of Formula 11, wherein X is a metal-containing moiety and Y is a leaving group,

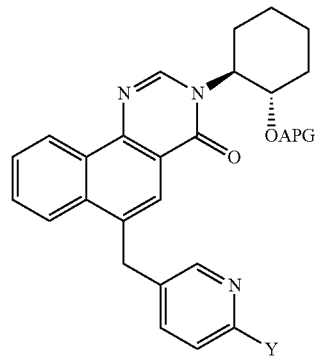
11 alkylating the compound of structural Formula 11 using a alkylating reagent to provide a compound of Formula 12:

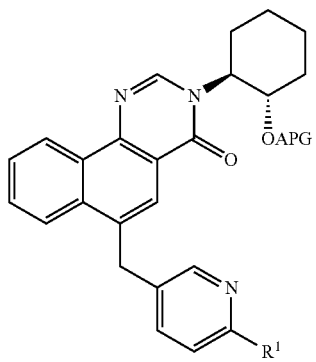

by way of step (1) or step (2) wherein:
step (1) comprises adding the alkylating reagent to the reaction mixture comprising the compound of Formula 11 without further isolation to make a compound of Formula 12, or step (2) comprises isolating the compound of Formula 11 and reacting it with the alkylating reagent in the presence of a first palladium catalyst complex to provide a compound of Formula 12, and deprotecting the alcohol protecting group in the compound of Formula 12 and isolating a compound of Formula I.

2. The process of claim 1 wherein the alcohol protecting group is selected from the group consisting of tert-butyldimethylsilyl, trimethylsilyl, acetyl, and tetrahydropyranyl.

3. The process of claim 1 wherein the first palladium catalyst complex is selected from the group consisting of PCy3-G2-palladacycle (Chloro[(tricyclohexylphosphine)-2-(2'-aminobiphenyl)]palladium(II)), $(Pd(tBu_3P)_2$, $Pd_2dba_3$, $Pd_2dba_3\text{-}CHCl_3$, $Pd(OAc)_2$, $Pd(dba)_2$, $Pd(TFA)_2$, $Pd(MeCN)_2Cl_2$, Pd(allyl)Cl dimer, Pd(cinnamyl)Cl dimer (Bis[cinnamyl palladium(II) chloride]), Pd(aminobiphenyl)Cl dimer ((2'-amino-[1,1'-biphenyl]-2-yl)palladium(II) chloride dimer), and Pd(aminobiphenyl)OMs dimer ((2'-amino-[1,1'-biphenyl]-2-yl)palladium(II) methanesulfonate).

4. The process of claim 3 wherein the first palladium catalyst complex is selected from the group consisting of $Pd(tBu_3P)_2$, $Pd_2dba_3$ and $Pd_2dba_3\text{-}CHCl_3$.

5. The process of claim 1 wherein the leaving group is selected from the group consisting of halogen, $OSO_2R^\wedge$, OMs (mesylate), OTs (tosylate), OBs (besylate), $OSO_2CF_3$ (OTf), $OSO_2CF_2CF_2CF_2CF_3$, $OP(O)(OR^i)_4$, $OC(O)R^i$, $OC(O)OR^i$ and $OC(O)NR^iR^{ii}$, wherein $R^\wedge$ is selected from the group consisting of $C_{1-6}$ alkyl, $C_{1-4}$ fluoroalkyl, and $C_{6-10}$ aryl, $R^i$ and $R^{ii}$ are independently selected from H, $C_{1-6}$alkyl, and $C_{1-4}$ fluoroalkyl; and the metal-containing moiety is selected from the group consisting of Li, MgCl, MgBr, MgI, ZnCl, ZnBr, ZnI, $SnMe_3$, $Sn(n\text{-}Bu)_3$, $B(OH)_2$, $B(OR)_2$, B(pinacol), B(N-methyliminoacetate), and $BF_3K$.

6. The process of claim 5 wherein the leaving group is selected from the group consisting of chloro, bromo, fluoro, and iodo and the metal-containing moiety is selected from the group consisting of ZnCl, ZnBr, and ZnI.

7. The process of claim 1 wherein the alkylating reagent is selected from the group consisting of MeZnCl, $Me_2Zn$, $MeB(OH)_2$, $MeMgCl/ZnCl_2$, $MeLi/ZnCl_2$, and $SnMe_4$.

8. The process of claim 7 wherein the alkylating reagent is MeZnCl.

9. The process of claim 1 wherein alkylation is performed using step (1).

10. The process of claim 1 wherein alkylation is performed using step (2).

11. The process of claim 1 wherein the alcohol protecting group is tert-butyldimethylsilyl or trimethylsilyl, the first palladium catalyst complex is $Pd(tBu_3P)_2$, the leaving group is selected from the group consisting of chloro, bromo, and fluoro, the metal-containing moiety is selected from the group consisting of ZnCl, and the alkylating reagent is MeZnCl.

12. A process for the preparation of a compound of formula I:

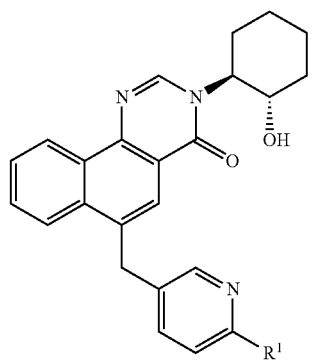

(I)

or a pharmaceutically acceptable salt thereof, wherein $R^1$ is $C_{1-6}$ alkyl, comprising:
contacting a compound of formula 8:

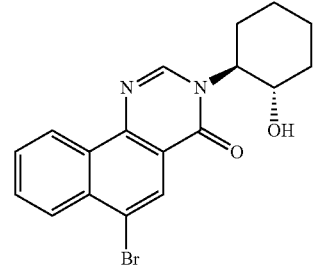

8 with a borylating agent in the presence of a second palladium catalyst complex, optionally a second ligand, and an inorganic base make a compound of Formula 9A:

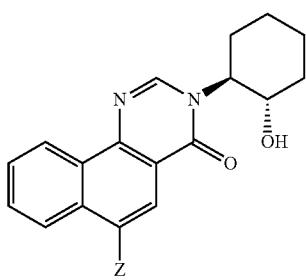

9A wherein Z is selected from the group consisting of B(pinacol), $B(OH)_2$, $BF_3K$, and B(N-methyliminoacetate), coupling compound of Formula 9A with a compound of Formula 10A:

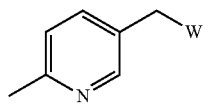
10A wherein W is OCOR$^W$ and R$^W$ is C$_{1-6}$ alkyl, or C$_{1-4}$ haloalkyl, in the presence of a third palladium catalyst complex, optional third ligand and an inorganic base to produce a compound of Formula I.

13. The process of claim 12 wherein the second and third palladium catalyst complex is selected from the group consisting of PCy3-G2-palladacycle (Chloro[(tricyclohexylphosphine)-2-(2'-aminobiphenyl)]palladium(II)), (Pd(tBu$_3$P)$_2$, Pd$_2$dba$_3$-CHCl$_3$, Pd(OAc)$_2$, Pd(dba)$_2$, Pd(TFA)$_2$, Pd(MeCN)$_2$Cl$_2$, Pd(allyl)Cl dimer, Pd(cinnamyl)Cl dimer (Bis[cinnamyl palladium(II) chloride]), Pd(aminobiphenyl)Cl dimer ((2'-amino-[1,1'-biphenyl]-2-yl)palladium(II) chloride dimer), and Pd(aminobiphenyl)OMs dimer ((2'-amino-[1,1'-biphenyl]-2-yl)palladium(II) methanesulfonate).

14. The process of claim 12 wherein the borylating agent is a compound of Formula B or B':

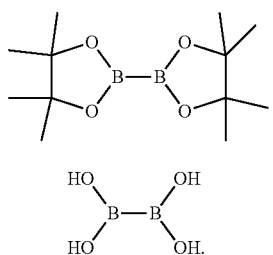

B

B'

15. The process of claim 12 wherein Z is B(pinacol).
16. The process of claim 12 wherein Z is B(OH)$_2$.
17. The process of claim 12 wherein 9A solution contains a mixture of 9A with B(pinacol) and 9A with B(OH)$_2$.
18. The process of claim 12 wherein the second palladium catalyst complex is PCy3-G2-palladacycle.
19. The process of claim 12 wherein the inorganic base is selected from the group consisting of KOAc, K$_2$CO$_3$, K$_3$PO$_4$, KF, Cs$_2$CO$_3$, KOH, NaOH, LiOH, DIPEA, KHCO$_3$, and NaHCO$_3$.

20. The process of claim 12 wherein in the coupling of 9A and 10A step the third palladium catalyst complex is Pd(OAc)$_2$, a third ligand is present which is RuPhos, and an inorganic base is present which is K$_2$CO$_3$.

21. A process for the preparation of a compound of formula I:

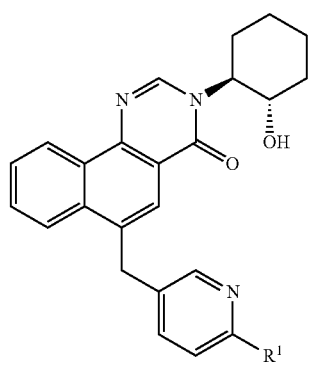
(I)

or a pharmaceutically acceptable salt thereof, wherein R$^1$ is C$_{1-6}$ alkyl, comprising deprotecting a compound of Formula 12:

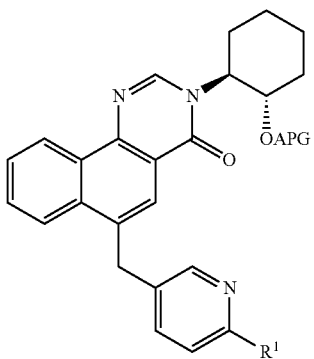
12 and isolating a compound of Formula I, wherein APG is alcohol protecting group.

* * * * *